United States Patent [19]
Minato et al.

[11] 3,932,421
[45] Jan. 13, 1976

[54] PROCESS FOR PRODUCING ALKYLPYRIDINES

[75] Inventors: Yoshizo Minato, Nishinomiya; Shinichi Yasuda, Otsu, both of Japan

[73] Assignee: Koei Chemical Company, Ltd., Osaka, Japan

[22] Filed: July 2, 1971

[21] Appl. No.: 159,548

Related U.S. Application Data

[63] Continuation-in-part of Ser. No. 743,023, July 8, 1968, abandoned.

[30] Foreign Application Priority Data

July 13, 1967 Japan.............................. 42-45158

[52] U.S. Cl. .............................. 260/290 P; 252/435
[51] Int. Cl.²........................................ C07C 213/10
[58] Field of Search..................................... 260/290

[56] References Cited
UNITED STATES PATENTS

| | | | |
|---|---|---|---|
| 2,523,580 | 9/1950 | Mahan................................ | 260/290 |
| 3,381,011 | 4/1968 | Hall..................................... | 260/290 |
| 3,433,792 | 3/1969 | Adams et al........................ | 260/290 |

FOREIGN PATENTS OR APPLICATIONS

| | | | |
|---|---|---|---|
| 641,331 | 5/1962 | Canada............................... | 260/290 |
| 742,643 | 12/1955 | United Kingdom................. | 260/290 |
| 758,076 | 9/1956 | United Kingdom................. | 260/290 |

OTHER PUBLICATIONS

Adams et al., I, Brennstoff Chemie, Vol. 47, pp. 184–187, (1966).

Tschitschibabin, J. Prakt. Chemie, Vol. 107, pp. 122–128, (1924).

*Primary Examiner*—Harry I. Moatz
*Attorney, Agent, or Firm*—Stevens, Davis, Miller & Mosher

[57] ABSTRACT

Alkylpyridines such as 2-picoline and 4-picoline are prepared by contacting acetaldehyde and ammonia in a gaseous phase with a phosphate of two metals such as cobalt magnesium phosphate, cobalt aluminum phosphate or lead aluminum phosphate, impregnated with an aqueous solution of phosphoric acid or ammonium phosphate, as a catalyst, at a temperature of 350° to 500°C and a space velocity of 200 to 2,000 $Hr^{-1}$. Silica-alumina and a promoter can be added to the catalyst. The impregnated catalyst has a higher catalytic activity and holds the initial high activity even after a considerable number of regeneration.

12 Claims, No Drawings

PROCESS FOR PRODUCING ALKYLPYRIDINES

This is a continuation-in-part application of Pat. application Ser. No. 743,023 filed on July 8, 1968 and now abandoned.

This invention relates to a process for producing alkylpyridine bases by gaseous phase catalytic reaction of acetaldehyde with ammonia by using a novel catalyst, and more particularly to a process for producing alkylpyridine bases from acetaldehyde and ammonia by gaseous phase catalystic reaction, which comprises reacting the acetaldehyde with the ammonia in the presence of a catalyst prepared by impregnating a phosphate of two metals such as cobalt aluminum phosphate, cobalt magnesium phosphate and lead aluminum phosphate with an aqueous solution of phosphoric acid or ammonium phosphate thereby to selectively obtain 2-picoline in preference to 4-picoline.

Many processes have been so far proposed for producing 2-picoline and 4-picoline from acetaldehyde and ammonia in a gaseous phase over a catalyst having an ability to effect dehydration and dehydrogenation. Their reaction mechanism is generally given below:

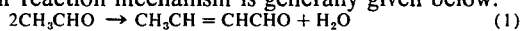

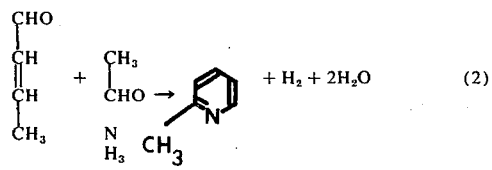

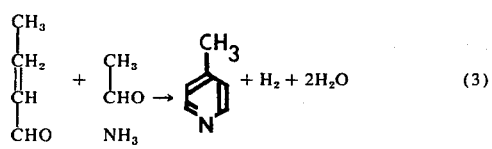

According to the above formulae, formation of 2-picoline or 4-picoline from acetaldehyde and ammonia depends upon whether $NH_3$ is combined with the unsaturated carbon at the $\beta$-position or with the carbon of the aldehyde radical.

The conventional catalyst used in the prior art process for producing 2-picoline and 4-picoline has produced 2-picoline and 4-picoline in almost equal proportion. For example, according to almost all the examples of Japanese Pat. No. 8356/65, the ratio of formation of 2-picoline to 4-picoline by mole is 1.2 on average and only 1.6 at a maximum.

According to "Synthesis of $\alpha$- and $\gamma$-picolines by gaseous phase catalytic reaction of paraaldehyde with ammonia, Report No. 2" (Bulletin of Government Chemical Industrial Research Institute, Tokyo, 58th Report, No. 10, pages 453 – 454), the ratio of formation of 2-picoline to 4-picoline by mole is 0.8 to 1.07.

However, a demand for 2-picoline as a tyrecord adhesive, herbicide, fertilizer additive and raw material for medicines for domestic animal has been recently vigorously increased, whereas a demand for 4-picoline has been limited only to a narrow market as medicine. Therefore, the conventional processes for producing 2-picoline and 4-picoline in almost equal amounts have failed to meet the market demand. That is to say, a process or catalyst capable of producing 2-picoline selectively in high yield has been so far desired.

An object of the present invention is to provide a catalyst capable of producing 2-picoline selectively in the gaseous phase catalytic reaction of acetaldehyde and ammonia.

According to the present invention, 2-picoline can be selectively produced from acetaldehyde and ammonia at a ratio of formation of 2-picoline to 4-picoline of about 4 – 5 : 1 by mole, when a phosphate of two metals such as cobalt aluminum phosphate, cobalt magnesium phosphate and lead aluminum phosphate impregnated with an aqueous solution of phosphoric acid or ammonium phosphate is used as a catalyst.

Further, according to the present invention, 2-picoline can be produced in higher yield, for example, at a ratio of formation of 2-picoline to 4-picoline of 1 – 5 : 1 by mole in correspondence to a mixing ratio when the phosphate of two metals impregnated with the aqueous solution of phosphoric acid or ammonium phosphate is mixed with silica-alumina and used as a catalyst.

Furthermore, by admixing the silica-alumina with a promoter, the yield can be much improved, as compared with the case where the mixture of the phosphate of two metals only with the silica-alumina is used.

In the present invention, the impregnation of the phosphate of two metals with the aqueous solution of phosphoric acid or ammonium phosphate has a remarkable effect upon an increase in the catalytic activity and maintenance of the initial catalytic activity, and furthermore can shorten a regeneration time for reactivating the catalytic activity.

On the other hand, when the phosphate of two metals is not impregnated with the aqueous solution of phosphoric acid or ammonium phosphate, the yield is low even at the initial stage of the reaction, and the yield is considerably lowered by repetitions of the reaction and regeneration. The regeneration time for the catalyst is also prolonged.

For example, Table A shows the yields obtained by 10 repetitions of the reaction and regeneration by using the phosphate of two metals having a composition of $Co_3Al_3(PO_4)_5$ without the impregnation with the aqueous solution of phosphoric acid or ammonium phosphate as a catalyst. It is shown that the first yield is 64.7 %, whereas the yields are gradually decreased with the repetitions of reaction and regeneration and finally the tenth yield is considerably lowered to 43.3 %.

Table A

| Products | Reaction Run | | | | | |
|---|---|---|---|---|---|---|
| | 1st | wnd | 3rd | 4th | 5th | 10th |
| pyridine | 2.4 % | 2.1 % | 1.6 % | 1.5 % | 1.2 % | 0.8 % |
| 2-picoline | 42.8 | 40.3 | 37.8 | 36.2 | 34.3 | 30.2 |
| 4-picoline | 8.9 | 8.5 | 8.0 | 7.6 | 7.1 | 6.3 |
| 2-methyl-3-ethyl pyridine | 4.5 | 4.1 | 3.7 | 3.2 | 2.9 | 2.1 |
| 2-methyl-5-ethyl pyridine | 6.1 | 5.9 | 5.4 | 5.2 | 4.8 | 3.9 |
| Overall yield | 64.7 % | 60.9 % | 56.5 % | 53.7 % | 50.3 % | 43.3 % |

Table A-continued

| Products | Reaction Run | | | | | |
|---|---|---|---|---|---|---|
| | 1st | wnd | 3rd | 4th | 5th | 10th |
| Ratio of formation of 2-picoline to 4-picoline | 4.8 | 4.75 | 4.75 | 4.8 | 4.8 | 4.8 |
| Regeneration time (hr) | 4.0 | 4.5 | 4.5 | 4.5 | 4.5 | 4.5 |

On the other hand, Table B shows the yields obtained by 20 repetitions of reaction and regeneration by using a catalyst prepared by impregnating 500 g of $Co_3Al_3(PO_4)_5$ with 350 g of an aqueous solution of 8 % by weight of phosphoric acid. It is shown that the first yield is 68.6 %, and the initial catalytic activity is higher, as compared with that of the catalyst without the impregnation with the aqueous phosphoric acid solution. It is seen that, even by 20 repetitions of reaction and regeneration, the yield can be kept at 68.4 % and the initial catalytic activity can be maintained.

The reaction can be effected under any desired pressure.

Now, the present invention will be explained in detail, referring to the examples. The yields used in the present specification are defined by the following formula:

$$\text{Yield (\%)} = \frac{\text{Carbon content of the pyridine base formed}}{\text{Carbon content of the starting material aldehyde}} \times 100$$

Table B

| Products | Reaction Run | | | | | |
|---|---|---|---|---|---|---|
| | 1st | 2nd | 3rd | 7th | 12th | 20th |
| pyridine | 2.6 % | 2.3 % | 2.8 % | 2.7 % | 2.3 % | 2.5 % |
| 2-picoline | 45.5 | 45.1 | 45.3 | 45.6 | 45.2 | 45.4 |
| 4-picoline | 9.5 | 9.1 | 9.3 | 8.8 | 9.3 | 9.3 |
| 2-methyl-3-ethyl pyridine | 4.9 | 5.1 | 4.6 | 5.0 | 4.7 | 4.9 |
| 2-methyl-5-ethyl pyridine | 6.3 | 6.5 | 6.2 | 6.7 | 6.3 | 6.3 |
| Overall yield | 68.6 % | 68.1 % | 68.2 % | 68.8 % | 67.8 % | 68.4 % |
| Ratio of formation of 2-picoline to 4-picoline | 4.8 | 4.95 | 4.9 | 5.2 | 4.85 | 4.85 |
| Regeneration time (hr) | 2.5 | 3.0 | 3.0 | 3.0 | 3.0 | 3.0 |

In carrying out the present invention, it is preferable to impregnate phosphate of two metals with an aqueous solution of 1 to 30 % by weight of phosphoric acid or ammonium phosphate on the basis of the phosphate of two metals. Further, it is preferable to use an aqueous solution of 1 to 25 % by weight of phosphoric acid or 1 to 35 % by weight of ammonium phosphate as the impregnating solution.

As the ammonium phosphate, any of monoammonium dihydrogenphosphate, di-ammonium monohydrogenphosphate and triammonium phosphate can be used in the present invention.

In carrying out the present invention, $Co_3Al(PO_4)_3$, $Co_3Al_2(PO_4)_4$, $Co_3Al_3(PO_4)_5$, $Co_3Al_5(PO_4)_7$, etc. can be used as cobalt aluminum phosphate; $Co_3Mg_3(PO_4)_5$ can be used as cobalt magnesium phosphate; $Pb_3Al_5(PO_4)_7$ can be used as lead aluminum phosphate. In any case, good results can be obtained.

When the phosphate of two metals is admixed with silica-alumina to control the ratio of formation of 2-picoline to 4-picoline, the yield can be improved by adding at least one of promoters such as lead oxide, cadmium oxide, lead fluoride, manganese fluoride and bismuth fluoride to the silica-alumina.

In carrying out the present invention, it is desirable to react acetaldehyde with ammonia in a gaseous state at a molar ratio of acetaldehyde to ammonia of 1 : 0.3 – 3 in the presence of said catalyst at a reaction temperature of 350° to 500°C and a space velocity (S.V.) of 200 to 2000 $hr^{+1}$. It is desirable to contact acetaldehyde with ammonia at least at 200°C.

Any of a fixed bed, fluidized bed or moving bed type can be employed to carry out the present invention.

EXAMPLE 1

4,800 g of an aqueous solution containing 4.8 moles of diammonium monohydrogenphosphate and 8,800 g of an aqueous solution containing 3 moles of cobalt nitrate and 2 moles of aluminum nitrate were mixed instantaneously at a temperature of 45°C, whereby a phosphate of two metals having a composition of $Co_3Al_2(PO_4)_4$ was precipitated. After the solution was neutralized with ammonia water, the precipitates were thoroughly washed with water and dried. 500 g of the thus dried precipitates were impregnated with 300 g of an aqueous solution of 3 % by weight of phosphoric acid, dried and molded to pellets having diameters of 3 mm. 500 cc of the thus prepared pellets was packed in a reactor of stainless steel having an inner diameter of 20 mm and a height of 3000 mm as a catalyst.

350 g/hr of acetaldehyde and 140 g/hr of ammonia, which were preheated separately to 400°C, were mixed, and the resulting mixture was passed through the reactor for 3 hours, while keeping the reactor at a temperature of 450°C.

The reaction liquid was cooled and sufficiently dehydrated with flaky caustic soda, and fractionated in a distilling column. After the completion of the reaction, $N_2$ gas was passed through the reactor to flush the reactor with $N_2$ gas sufficiently, and then a gas mixture of air and steam was passed through the reactor. Carbonaceous materials deposited on the catalyst during the reaction was combusted at a temperature of 500° to 520°C to regenerate the activity of the catalyst. The yields and the ratios of formation of 2-picoline to 4-picoline when the reactions and regenerations were repeated five times are shown in Table 1.

For comparison, the results obtained when the powders of $Co_3Al_2(PO_4)_4$ without any impregnation with the aqueous phosphoric acid solution was used as the catalyst are shown in Table 2.

pregnated with 600 g of an aqueous solution of 10 % by weight of monoammonium dihydrogenphosphate, dried and molded to pellets having diameters of 3 mm. 500 cc of the thus prepared pellets was packed in a Table 1

| Yield | Reaction Run | | | | |
|---|---|---|---|---|---|
| | 1st | 2nd | 3rd | 4th | 5th |
| pyridine | 3.5 % | 2.9 % | 3.1 % | 3.0 % | 3.8 % |
| 2-picoline | 40.6 " | 43.7 " | 43.9 " | 43.7 " | 42.6 % |
| 4-picoline | 9.6 " | 9.9 " | 9.9 " | 9.7 " | 9.5 " |
| 2-methyl-3-ethyl-pyridine | 3.7 " | 4.2 " | 4.5 " | 4.5 " | 4.1 " |
| 2-methyl-5-ethyl-pyridine | 7.8 " | 7.3 " | 7.4 " | 7.8 " | 7.2 " |
| Overall yield | 65.2 % | 68.0 % | 68.8 % | 68.7 % | 67.2 % |
| Ratio of formation of 2-picoline to 4-picoline | 4.24 | 4.4 | 4.4 | 4.5 | 4.5 |
| Regeneration time (hr) | 3.0 | 3.5 | 3.5 | 3.5 | 3.5 |

Table 2

| Yield | Reaction Run | | | | |
|---|---|---|---|---|---|
| | 1st | 2nd | 3rd | 4th | 5th |
| pyridine | 2.8 % | 2.3 % | 2.2 % | 1.6 % | 1.2 % |
| 2-picoline | 40.0 " | 39.6 " | 38.3 " | 37.1 " | 36.6 " |
| 4-picoline | 9.3 " | 9.0 " | 8.8 " | 8.3 " | 8.1 " |
| 2-methyl-3-ethyl-pyridine | 3.5 " | 3.3 " | 2.9 " | 2.8 " | 2.2 " |
| 2-methyl-5-ethyl-pyridine | 6.6 " | 6.7 " | 6.0 " | 5.7 " | 5.1 " |
| Overall yield | 62.2 % | 60.9 % | 58.2 % | 55.5 % | 53.2 % |
| Ratio of formation of 2-picoline to 4-picoline | 4.3 | 4.5 | 4.35 | 4.45 | 4.5 |
| Regeneration time (hr) | 4.0 | 4.5 | 4.5 | 4.5 | 4.5 |

EXAMPLE 2

$Co_3Mg_3(PO_4)_4$ was prepared from 4,800 g of an aqueous solution containing 4.8 moles of diammonium monohydrogenphosphate and 8,800 g of an aqueous solution containing 3 moles of cobalt nitrate and 3 moles of magnesium nitrate in the same manner as in Example 1, and thoroughly washed with water and dried. 500 g of the thus dried $Co_3Mg_3(PO_4)_4$ was imreactor tube as a catalyst, and the reactions and regenerations were repeated 5 times under the same reaction and regeneration conditions as in Example 1. The yields and ratios of formation of 2-picoline to 4-picoline are shown in Table 3.

For comparison, the results obtained when the $Co_3Mg_3(PO_4)_4$ without any impregnation with the aqueous solution of monoammonium dihydrogenphosphate was used as a catalyst are shown in Table 4.

Table 3

| Yields | Reaction Run | | | | |
|---|---|---|---|---|---|
| | 1st | 2nd | 3rd | 4th | 5th |
| pyridine | 2.5 % | 2.3 % | 2.7 % | 2.4 % | 2.6 % |
| 2-picoline | 44.3 " | 44.1 " | 43.9 " | 44.6 " | 44.0 " |
| 4-picoline | 9.2 " | 9.4 " | 9.0 " | 9.1 " | 9.2 " |
| 2-methyl-3-ethyl-pyridine | 4.9 " | 4.6 " | 4.8 " | 5.2 " | 4.7 " |
| 2-methyl-5-ethyl-pyridine | 8.0 " | 7.6 " | 7.7 " | 7.1 " | 7.8 " |
| Overall yield | 68.9 % | 68.0 % | 68.1 % | 68.4 % | 68.3 % |
| Ratio of formation of 2-picoline to 4-picoline | 4.8 | 4.7 | 4.9 | 4.9 | 4.8 |
| Regeneration time (hr) | 3 | 3.5 | 3 | 3.5 | 3.5 |

Table 4

| Yields | Reaction Run | | | | |
|---|---|---|---|---|---|
| | 1st | 2nd | 3rd | 4th | 5th |
| pyridine | 2.3 % | 2.0 % | 1.6 % | 1.3 % | 1.1 % |
| 2-picoline | 42.8 " | 39.8 " | 37.2 " | 35.6 " | 33.3 " |
| 4-picoline | 8.9 " | 8.3 " | 7.8 " | 7.4 " | 6.9 " |
| 2-methyl-3-ethyl-pyridine | 4.5 " | 3.9 " | 3.4 " | 2.9 " | 2.7 " |
| 2-methyl-5-ethyl-pyridine | 8.1 " | 7.1 " | 6.6 " | 5.9 " | 5.3 " |
| Overall yield | 66.6 % | 61.1 % | 56.6 % | 53.1 % | 49.3 % |

Table 4-continued

| Yields | 1st | 2nd | Reaction Run 3rd | 4th | 5th |
|---|---|---|---|---|---|
| Ratio of formation of 2-picoline to 4-picoline | 4.8 | 4.9 | 4.8 | 4.8 | 4.8 |
| Regeneration time (hr) | 4 | 4.5 | 4.5 | 4.5 | 4.5 |

EXAMPLE 3

$Co_3Al_3(PO_4)_5$ was prepared from 3,000 g of an aqueous solution containing 5.5 moles of diammonium monohydrogenphosphate and 8,800 g of an aqueous solution containing 3 moles of cobalt nitrate and 3 moles of aluminum nitrate in the same manner as in Example 1, thoroughly washed with water and dried. 500 g of the thus dried $Co_3Al_3(PO_4)_5$ was impregnated with 550 g of an aqueous solution containing 8 % by weight of phosphoric acid, dried and molded to pellets having diameters of 3 mm. 500 cc of the thus prepared pellets was packed in a reactor tube of stainless steel having an inner diameter of 20 mm and height of 3,000 mm as a catalyst, and reactions and regenerations were repeated 5 times under the same reaction and regeneration conditions as in Example 1. The yields and the ratios of formation of 2-picoline to 4-picoline are shown in Table 5.

For comparison, the results obtained when the $Co_3Al_3(PO_4)_5$ without any impregnation with the aqueous phosphoric acid solution was used as a catalyst are shown in Table 6.

EXAMPLE 4

$Pb_3Al_5(PO_4)_7$ was prepared from 12,000 g of an aqueous solution containing 8.4 moles of diammonium monohydrogenphosphate and 5,000 g of 3 moles of lead acetate and 5 moles of aluminum nitrate in the same manner as in Example 1, washed with water and dried. 500 g of the thus dried powders of $Pb_3Al_5(PO_4)_7$ was impregnated with 800 g of an aquoues solution containing 12 % by weight of triammonium phosphate, dried and molded to pellets having diameters of 3 mm. 500 cc of the thus prepared pellets was packed in a reactor tube of stainless steel having an inner diameter of 20 mm and height of 3,000 mm, and reactions and regenerations were repeated 7 times under the same reaction and regeneration conditions as in Example 1. The yields and ratios of formation of 2-picoline to 4-picoline are shown in Table 7.

For comparison, the results obtained when the $Pb_3Al_5(PO_4)_7$ without any impregnation with the aqueous triammonium phosphate solution was used as a catalyst are shown in Table 8.

Table

| Yields | 1st | 2nd | Reaction Run 3rd | 4th | 5th |
|---|---|---|---|---|---|
| pyridine | 2.6 % | 2.3 % | 2.8 % | 2.7 % | 2.1 % |
| 2-picoline | 45.5 " | 45.1 " | 45.3 " | 45.4 " | 45.0 " |
| 4-picoline | 9.5 " | 9.1 " | 9.3 " | 8.9 " | 9.4 " |
| 2-methyl-3-ethyl-pyridine | 4.9 " | 5.1 " | 4.6 " | 4.9 " | 4.1 " |
| 2-methyl-5-ethyl-pyridine | 6.3 " | 6.5 " | 6.2 " | 6.7 " | 7.1 " |
| Overall yield | 68.8 % | 68.1 % | 68.2 % | 68.6 % | 67.7 % |
| Ratio of formation of 2-picoline to 4-picoline | 4.8 | 4.95 | 4.9 | 5.1 | 4.8 |
| Regeneration time (hr) | 2.5 | 3.0 | 3.0 | 3.5 | 3.5 |

Table 6

| Yields | 1st | 2nd | Reaction Run 3rd | 4th | 5th |
|---|---|---|---|---|---|
| pyridine | 2.4 % | 2.1 % | 1.6 % | 1.5 % | 1.2 % |
| 2-picoline | 42.8 " | 40.3 " | 37.8 " | 36.2 " | 34.3 " |
| 4-picoline | 8.9 " | 8.5 " | 8.0 " | 7.6 " | 7.1 " |
| 2-methyl-3-ethyl-pyridine | 4.5 " | 4.1 " | 3.7 " | 3.2 " | 2.9 " |
| 2-methyl-5-ethyl-pyridine | 6.1 " | 5.9 " | 5.4 " | 5.2 " | 4.8 " |
| Overall yield | 64.7 % | 60.9 % | 56.5% | 53.7 % | 50.3 % |
| Ratio of formation of 2-picoline to 4-picoline | 4.8 | 4.75 | 4.75 | 4.8 | 4.8 |
| Regeneration time (hr) | 4 | 4.5 | 4.5 | 4.5 | 4.5 |

Table 7

| Yields | 1st | 2nd | Reaction Run 3rd | 4th | 5th | 7th |
|---|---|---|---|---|---|---|
| pyridine | 3.0 % | 2.6 % | 2.6 % | 2.3 % | 2.0 % | 2.7 % |
| 2-picoline | 42.9 " | 42.7 " | 42.2 " | 42.4 " | 42.6 " | 41.9 " |
| 4-picoliine | 8.4 " | 8.3 " | 8.6 " | 8.4 " | 8.6 " | 8.7 " |
| 2-methyl-3-ethyl- | | | | | | |

Table 7-continued

| Yields | 1st | 2nd | Reaction Run 3rd | 4th | 5th | 7th |
|---|---|---|---|---|---|---|
| pyridine | 5.0 " | 5.2 " | 5.4 " | 5.5 " | 5.3 " | 5.7 " |
| 2-methyl-5-ethyl-pyridine | 7.2 " | 7.6 " | 7.3 " | 7.5 " | 7.1 " | 7.5 " |
| Overall yield | 66.5 % | 66.4 % | 66.1 % | 66.1 % | 66.2 % | 66.5 % |
| Ratio of formation of 2-picoline to 4-picoline | 5.1 | 5.15 | 4.9 | 5.05 | 4.95 | 4.8 |
| Regeneration time (hr) | 3.5 | 4.0 | 4.0 | 4.0 | 4.0 | 4.0 |

Table 8

| Yields | 1st | 2nd | Reaction Run 3rd | 4th | 5th |
|---|---|---|---|---|---|
| pyridine | 2.4 % | 2.1 % | 1.5 % | 1.1 % | 0.7 % |
| 2-picoline | 41.2 " | 39.6 " | 38.1 " | 35.3 " | 33.2 " |
| 4-picoline | 7.9 " | 7.2 " | 7.1 " | 6.8 " | 6.4 " |
| 2-methyl-3-ethyl-pyridine | 4.6 " | 4.3 " | 4.2 " | 3.9 " | 3.2 " |
| 2-methyl-5-ethyl-pyridine | 6.9 " | 6.7 " | 6.2 " | 6.0 " | 5.2 " |
| Overall yield | 63.0 % | 59.9 % | 57.1 % | 53.1 % | 48.7 % |
| Ratio of formation of 2-picoline to 4-picoline | 5.2 | 5.5 | 5.35 | 5.2 | 5.2 |
| Regeneration time (hr) | 4.5 | 5.0 | 5.0 | 5.0 | 5.0 |

EXAMPLE 5

An aqueous sodium silicate solution was neutralized with sulfuric acid, and to the precipitated silica gel was added an aqueous aluminum nitrate solution. Ammonia water was added thereto, while sufficiently stirring the gel mixture, and aluminum hydroxide was precipitated, washed with water, dried and fired at 600°C for 2 hours, whereby silica-alumina powders having 82 % $SiO_2$ and 18 % $Al_2O_3$ was obtained. 150 g of the thus obtained silica-alumina powders and 350 g of $Pb_3Al_5(PO_4)_7$ prepared in Example 4 and impregnated with 300 g of an aqueous solution containing 3 % by weight of phosphoric acid were mixed together and molded to pellets having diameters of 3 mm. 500 cc of the pellets were packed in the same reactor tube as in Example 1 as a catalyst, and reactions and regenerations were repeated 10 times under the same reaction and regeneration conditions. The results are shown in Table 9.

For comparison, 150 g of the silica-alumina powders of 82 % $SiO_2$ — 18 % $Al_2O_3$ and 350 g of the powders of $Pb_3Al_5(PO_4)_7$ without any impregnation with the aqueous phosphoric acid solution were mixed together and used as a catalyst. The results are shown in Table 10.

Table 9

| Yields | 1st | 3rd | Reaction Run 5th | 7th | 10th |
|---|---|---|---|---|---|
| pyridine | 3.1 % | 2.6 % | 2.9 % | 3.0 % | 2.4 % |
| 2-picoline | 39.8 " | 38.7 " | 39.1 " | 38.6 " | 39.3 " |
| 4-picoline | 15.9 " | 16.1 " | 16.3 " | 16.0 " | 16.2 " |
| 2-methyl-3-ethyl-pyridine | 3.4 " | 3.6 " | 3.2 " | 3.8 " | 3.5 " |
| 2-methyl-5-ethyl-pyridine | 5.5 " | 5.2 " | 4.9 " | 5.4 " | 5.0 " |
| Overall yield | 67.7 % | 66.2 % | 66.4 % | 66.8 % | 66.4 % |
| Ratio of formation of 2-picoline to 4-picoline | 2.5 | 2.4 | 2.4 | 2.4 | 2.4 |
| Regeneration time (hr) | 2.5 | 3.0 | 3.0 | 3.0 | 3.0 |

Table 10

| Yields | 1st | 2nd | Reaction Run 3rd | 5th | 7th |
|---|---|---|---|---|---|
| pyridine | 2.9 % | 2.6 % | 2.5 % | 2.4 % | 2.0 % |
| 2-picoline | 38.3 " | 37.8 " | 37.0 " | 35.8 " | 33.0 " |
| 4-picoline | 15.9 " | 15.1 " | 15.1 " | 14.9 " | 13.2 " |
| 2-methyl-3-ethyl-pyridine | 3.1 " | 2.6 " | 2.5 " | 2.2 " | 2.1 " |
| 2-methyl-5-ethyl-pyridine | 4.8 " | 4.2 " | 4.0 " | 3.7 " | 3.4 " |
| Overall yield | 65.0 % | 62.3 % | 61.1 % | 59.0 % | 53.7 % |
| Ratio of formation of 2-picoline to 4-picoline | 2.4 | 2.5 | 2.45 | 2.4 | 2.5 |
| Regeneration time (hr) | 3.0 | 3.5 | 4.0 | 4.0 | 4.0 |

EXAMPLE 6

An aqueous sodium silicate solution was neutralized with sulfuric acid, and to the thus precipitated silica gel were added an aqueous aluminum nitrate solution and an aqueous zinc nitrate solution. While the solution was further stirred thoroughly, ammonia water was added thereto, whereby aluminum hydroxide and zinc hydroxide were coprecipitated, washed with water, dried and fired at 500°C for 2 hours. 250 g of the thus obtained powders of 82 % $SiO_2$ — 13 % $Al_2O_3$ — 5 % ZnO, and 250 g of $Pb_3Al_5(PO_4)_7$ obtained in Example 4 and impregnated with 300 g of an aqueous solution containing 10 % by weight of phosphoric acid were mixed together and molded to pellets having diameters of 3 mm. 500 cc of the thus prepared pellets was packed in the same reactor tube as in Example 1, and reactions and regenerations were repeated thirty times under the same conditions as in Example 1. The yields and the ratios of 2-picoline to 4-picoline are shown in Table 11.

For comparison, the results obtained when 250 g of said powders of 82 % $SiO_2$ — 13 % $Al_2O_3$ — 5 % ZnO and 250 g of the powders of $Pb_3Al_5(PO_4)_7$ without any impregnation with the aqueous phosphoric acid solution were mixed together and used as a catalyst are shown in Table 12.

From the 7th reaction, a crystalline material began to adhere to a cooler of the reactor, and in the 16th reaction the crystalline material completely blocked up the cooler, whereby the reaction could not be continued any longer.

Table 11

| Yields | Reaction Run | | | | | Average yield for 1 – 30 runs |
|---|---|---|---|---|---|---|
|  | 1st | 5th | 10th | 15th | 20th |  |
| pyridine | 2.4 % | 2.2 % | 2.7 % | 2.6 % | 2.8 % | 2.5 % |
| 2-picoline | 38.7 " | 38.9 " | 38.4 " | 39.0 " | 38.6 " | 38.7 " |
| 4-picoline | 19.3 " | 19.2 " | 18.9 " | 19.4 " | 19.1 " | 19.2 " |
| 2-methyl-3-ethyl-pyridine | 4.2 " | 3.9 " | 4.6 " | 4.2 " | 3.8 " | 4.1 " |
| 2-methyl-5-ethyl-pyridine | 6.0 " | 6.2 " | 6.3 " | 5.9 " | 6.1 " | 6.1 " |
| Overall yield | 70.6 % | 70.4 % | 70.9 % | 71.1 % | 70.4 % | 70.6 % |
| Ratio of formation of 2-picoline to 4-picoline | 2.02 | 2.02 | 2.03 | 2.01 | 2.02 | 2.02 |
| Regeneration time (hr) | 2 | 2.5 | 2.5 | 2.5 | 2.5 | 2.5 |

Table 12

| Yields | Reaction Run | | | | | Average yield for 1 – 15 runs |
|---|---|---|---|---|---|---|
|  | 1st | 3rd | 7th | 10th | 15th |  |
| pyridine | 2.0 % | 1.7 % | 1.4 % | 1.2 % | 0.9 % | 1.3 % |
| 2-picoline | 37.0 " | 35.0 " | 32.1 " | 30.2 " | 28.8 " | 31.9 " |
| 4-picoline | 18.4 " | 17.3 " | 16.0 " | 15.1 " | 14.3 " | 15.8 " |
| 2-methyl-3-ethyl-pyridine | 3.6 " | 2.9 " | 2.3 " | 1.9 " | 1.6 " | 2.2 " |
| 2-methyl-5-ethyl-pyridine | 5.6 " | 4.8 " | 3.9 " | 2.9 " | 2.3 " | 3.7 " |
| Overall yield | 66.6 % | 61.7 % | 55.7 % | 51.3 % | 47.9 % | 54.9 % |
| Ratio of formation of 2-picoline to 4-picoline | 2.01 | 2.02 | 2.01 | 2.01 | 2.01 | 2.01 |
| Regeneration time (hr) | 3 | 3.5 | 3.5 | 3.5 | 3.5 | 3.5 |

EXAMPLE 7

An aqueous sodium silicate solution was neutralized with sulfuric acid, and to the precipitated silica gel were added an aqueous aluminum nitrate solution and an aqueous cadmium nitrate solution. Ammonia water was added thereto while stirring the solution, and aluminum hydroxide and cadmium hydroxide were coprecipitated, washed with water, dried and fired at 500°C for 2 hours. 200 g of the thus obtained powders of 73 % $SiO_2$ — 14 % $Al_2O_3$ — 13 % CdO, and 150 g of powders of $Pb_3Al_5(PO_4)_7$ prepared in Example 4, and 150 g of powders of $Co_3Al_2(PO_4)_4$ prepared in Example 1, the latter two being impregnated with 650 g of an aqueous solution of 8 % by weight of phosphoric acid, were mixed and molded to pellets having diameters of 3 mm.

500 cc of the thus obtained pellets was packed in the same reactor tube as in Example 1 as a catalyst, and reactions and regenerations were repeated 5 times under the same reaction and regeneration conditions as in Example 1. The results are shown in Table 13.

For comparison, the results obtained when 200 g of said powders of 73 % $SiO_2$ — 14 % $Al_2O_3$ — 13 % CdO and 150 g of the powders of $Pb_3Al_5(PO_4)_7$ and 150 g of the powders of $Co_2Al_2(PO_4)_4$ without any impregnation with the aqueous phosphoric acid solution were mixed together and used as a catalyst are shown in Table 14.

Table 13

| Yields | 1st | 2nd | Reaction Run 3rd | 4th | 5th |
|---|---|---|---|---|---|
| pyridine | 2.3 % | 2.6 % | 2.5 % | 2.7 % | 2.2 % |
| 2-picoline | 38.2 " | 38.4 " | 37.9 " | 38.3 " | 37.8 " |
| 4-picoline | 15.7 " | 15.6 " | 15.4 " | 15.7 " | 15.7 " |
| 2-methyl-3-ethyl-pyridine | 3.8 " | 3.6 " | 4.0 " | 3.7 " | 4.3 " |
| 2-methyl-5-ethyl-pyridine | 6.3 " | 6.7 " | 6.6 " | 6.2 " | 6.4 " |
| Overall yield | 66.3 % | 66.9 % | 66.4 % | 66.6 % | 66.4 % |
| Ratio of formation of 2-picoline to 4-picoline | 2.45 | 2.45 | 2.45 | 2.4 | 2.4 |
| Regeneration time (hr) | 2.5 | 2.5 | 3.0 | 3.0 | 3.0 |

Table 14

| Yields | 1st | 2nd | Reaction Run 3rd | 4th | 5th |
|---|---|---|---|---|---|
| pyridine | 2.1 % | 1.7 % | 1.2 % | 1.3 % | 1.2 % |
| 2-picoline | 37.2 " | 36.0 " | 34.3 " | 33.9 " | 32.9 " |
| 4-picoline | 15.2 " | 15.0 " | 14.3 " | 13.9 " | 13.7 " |
| 2-methyl-3-ethyl-pyridine | 3.4 " | 2.8 " | 2.6 " | 2.5 " | 2.2 " |
| 2-methyl-5-ethyl-pyridine | 5.7 " | 5.4 " | 5.0 " | 4.7 " | 4.6 " |
| Overall yield | 63.6 % | 60.9 % | 57.4 % | 56.3 % | 54.6 % |
| Ratio of formation of 2-picoline to 4-picoline | 2.45 | 2.4 | 2.4 | 2.45 | 2.40 |
| Regeneration time (hr) | 3.0 | 3.5 | 3.5 | 3.5 | 3.5 |

EXAMPLE 8

An aqueous sodium silicate solution was neutralized with sulfuric acid, and an aqueous aluminum nitrate solution and an aqueous zinc nitrate solution were added to the precipitated silica gel, whereby aluminum hydroxide and zinc hydroxide were coprecipitated. The coprecipitates were filtered and washed with water. The water-washed cake was admixed with water and further with an aqueous lead acetate solution and an aqueous potassium fluoride solution separately while stirring the solution. Lead fluoride was thereby precipitated, dried and then fired at 500°C for 2 hours. The fired precipitate powders had a composition of 75 % $SiO_2$ — 16 % $Al_2O_3$ — 5 % ZnO — 4 % $PbF_2$.

150 g of the thus obtained powders and 350 g of powders of $Co_3Al(PO_4)_3$ that were prepared from 4,000 g of an aqueous solution containing 3.6 moles of diammonium monohydrogenphosphate and 7,500 g of an aqueous solution containing 3 moles of cobalt nitrate and 1 mole of aluminum nitrate in the same manner as in Example 1, the latter being impregnated with 400 g of an aqueous solution containing 25 % by weight of diammonium monohydrogenphosphate, were mixed together and molded to pellets of diameters of 3 mm.

500 cc of the thus prepared pellets was packed in the same reactor tube as in Example 1 as a catalyst, and reactions and regenerations were repeated 15 times under the same reaction and regeneration conditions as in Example 1. The results are shown in Table 15.

For comparison, the results obtained when 150 g of the powders of 75 % $SiO_2$ — 16 % $Al_2O_3$ — 5 % ZnO — 4 % $PbF_2$ and 350 g of the powders of $Co_3Al(PO_4)_3$ without any treatment of the aqeuous diammonium monohydrogenphosphate solution were mixed together and used as a catalyst are shown in Table 16.

Table 15

| Yields | 1st | 2nd | Reaction Run 3rd | 7th | 15th |
|---|---|---|---|---|---|
| pyridine | 3.1 % | 2.6 % | 2.9 % | 2.5 % | 2.8 % |
| 2-picoline | 41.6 " | 40.9 " | 41.3 " | 41.8 " | 41.1 " |
| 4-picoline | 12.6 " | 12.8 " | 12.7 " | 12.4 " | 12.6 " |
| 2-methyl-3-ethyl-pyridine | 4.1 " | 4.3 " | 3.9 " | 4.1 " | 4.5 " |
| 2-methyl-5-ethyl-pyridine | 6.9 " | 6.5 " | 7.2 " | 6.2 " | 6.5 " |
| Overall yield | 68.3 % | 67.1 % | 68.0 % | 67.0 % | 67.5 % |
| Ratio of formation of 2-picoline to 4-picoline | 3.3 | 3.2 | 3.25 | 3.35 | 3.25 |
| Regeneration time (hr) | 2.0 | 2.5 | 2.0 | 2.5 | 2.5 |

Table 16

| Yields | Reaction Run | | | | |
|---|---|---|---|---|---|
| | 1st | 2nd | 3rd | 5th | 7th |
| pyridine | 2.7 % | 2.5 % | 2.1 % | 1.6 % | 1.1 % |
| 2-picoline | 39.6 " | 39.2 " | 38.0 " | 36.5 " | 34.0 " |
| 4-picoline | 12.0 " | 11.6 " | 11.2 " | 10.5 " | 10.0 " |
| 2-methyl-3-ethyl-pyridine | 3.9 " | 3.6 " | 3.4 " | 2.9 " | 2.9 " |
| 2-methyl-5-ethyl-pyridine | 6.2 " | 5.7 " | 5.4 " | 5.3 " | 4.9 " |
| Overall yield | 64.4 % | 62.6 % | 60.1 % | 56.8 % | 52.9 % |
| Ratio of formation of 2-picoline to 4-picoline | 3.3 | 3.4 | 3.4 | 3.2 | 3.4 |
| Regeneration time (hr) | 3.0 | 3.5 | 3.5 | 3.5 | 3.5 |

Table 17

| Yields | Reaction Run | | | | |
|---|---|---|---|---|---|
| | 1st | 2nd | 3rd | 4th | 5th |
| pyridine | 2.6 % | 2.3 % | 2.3 % | 2.4 % | 2.1 % |
| 2-picoline | 39.1 " | 39.7 " | 39.2 " | 38.7 " | 39.6 " |
| 4-picoline | 14.6 " | 14.3 " | 14.3 " | 14.7 " | 14.7 " |
| 2-methyl-3-ethyl-pyridine | 3.9 " | 3.7 " | 4.2 " | 4.6 " | 4.1 " |
| 2-methyl-5-ethyl-pyridine | 7.0 " | 6.4 " | 6.9 " | 6.5 " | 7.0 " |
| Overall yield | 67.2 % | 66.4 % | 66.9 % | 66.9 % | 67.5 % |
| Ratio of formation of 2-picoline to 4-picoline | 2.7 | 2.8 | 2.75 | 2.65 | 2.7 |
| Regeneration time (hr) | 2.0 | 2.5 | 2.5 | 2.5 | 2.5 |

Table 18

| Yields | Reaction Run | | | | |
|---|---|---|---|---|---|
| | 1st | 2nd | 3rd | 4th | 5th |
| pyridine | 2.2 % | 2.0 % | 1.6 % | 1.4 % | 0.9 % |
| 2-picoline | 38.1 " | 37.0 " | 35.2 " | 34.3 " | 32.9 " |
| 4-picoline | 14.0 " | 13.4 " | 12.9 " | 12.2 " | 11.6 " |
| 2-methyl-3-ethyl-pyridine | 3.6 " | 3.5 " | 3.2 " | 2.9 " | 2.8 " |
| 2-methyl-5-ethyl-pyridine | 6.2 " | 6.0 " | 5.5 " | 5.1 " | 5.0 " |
| Overall yield | 64.1 % | 61.9 % | 58.4 % | 55.9 % | 53.2 % |
| Ratio of formation of 2-picoline to 4-picoline | 2.7 | 2.75 | 2.7 | 2.8 | 2.85 |
| Regeneration time (hr) | 3.0 | 3.5 | 3.5 | 3.5 | 3.5 |

EXAMPLE 9

200 g of powders having a composition of 73 % $SiO_2$ — 15 % $Al_2O_3$ — 8 % CdO — 4 % $MnF_2$ prepared in the same manner as in Example 8, and 250 g of powders of $Co_3Al_5(PO_4)_7$ prepared from 12,000 g of an aqueous solution containing 8.4 moles of diammonium monohydrogenphosphate and 9,500 g of an aqueous solution containing 3 moles of cobalt nitrate and 5 moles of aluminum nitrate in the same manner as in Example 1, the latter being impregnated with 170 g of an aqueous solution of 18 % by weight of phosphoric acid were mixed together and molded to pellets of diameters of 3 mm. 500 cc of the thus obtained pellets was packed in the same reactor tube as in Example 1 as a catalyst, and reactions and regenerations were repeated 5 times under the same reaction and regeneration conditions as in Example 1. The results are shown in Table 17.

For comparison, 200 g of the powders of 73 % $SiO_2$ — 15 % $Al_2O_3$ — 8 % CdO — 4 % $MnF_2$ and 250 g of the powders of $Co_3Al_5(PO_4)_7$ without any impregnation with the aqueous phosphoric acid solution were mixed together and used as a catalyst. The results are shown in Table 18.

EXAMPLE 10

250 g of powders having a composition of 73 % $SiO_2$ — 15 % $Al_2O_3$ — 5 % ZnO — 7 % $BiF_3$ prepared in the same manner as in Example 8, and 200 g of powders of $Co_3Mg_3(PO_4)_4$ prepared in Example 2, the latter being impregnated with 400 g of an aqueous solution of 8 % by weight of diammonium monohydrogenphosphate solution were mixed together and molded to pellets having diameters of 3 mm. 500 cc of the thus prepared pellets was packed in the same reactor tube as in Example 1 as a catalyst, and reactions and regenerations were repeated five times under the same reaction and regeneration conditions as in Example 1. The results are shown in Table 19.

For comparison, 250 g of the powders having a composition of 73 % $SiO_2$ — 15 % $Al_2O_3$ — 5 % ZnO — 7 % $BiF_3$ and 200 g of the powders of $Co_3Mg_3(PO_4)_4$ without any impregnation with the aqueous diammonium monohydrogenphosphate solution were mixed and used as a catalyst. The results are shown in Table 20.

Table 19

| Yields | 1st | 2nd | Reaction Run 3rd | 4th | 5th |
|---|---|---|---|---|---|
| pyridine | 2.1 % | 2.3 % | 1.9 % | 2.0 % | 2.3 % |
| 2-picoline | 37.8 " | 38.1 " | 37.9 " | 38.0 " | 37.6 " |
| 4-picoline | 23.6 " | 23.5 " | 23.1 " | 23.2 " | 23.1 " |
| 2-methyl-3-ethyl-pyridine | 3.3 " | 3.0 " | 3.5 " | 3.4 " | 3.1 " |
| 2-methyl-5-ethyl-pyridine | 5.0 " | 4.6 " | 5.9 " | 5.2 " | 5.4 " |
| Overall yield | 71.8 % | 71.5 % | 72.3 % | 71.8 % | 71.5 % |
| Ratio of formation of 2-picoline to 4-picoline | 1.6 | 1.6 | 1.65 | 1.65 | 1.65 |
| Regeneration time (hr) | 1.5 | 2.0 | 2.0 | 2.0 | 2.0 |

Table 20

| Yields | 1st | 2nd | Reaction Run 3rd | 4th | 5th |
|---|---|---|---|---|---|
| pyridine | 1.9 % | 1.8 % | 1.7 % | 1.3 % | 1.2 % |
| 2-picoline | 36.3 " | 35.6 " | 34.7 " | 33.4 " | 33.0 " |
| 4-picoline | 23.2 " | 21.6 " | 21.0 " | 19.6 " | 20.0 " |
| 2-methyl-3-ethyl-pyridine | 2.9 " | 2.7 " | 2.6 " | 2.4 " | 2.3 " |
| 2-methyl-5-ethyl-pyridine | 4.7 " | 4.3 " | 4.4 " | 4.0 " | 3.7 " |
| Overall yield | 69.0 % | 66.0 % | 64.4 % | 60.7 % | 60.2 % |
| Ratio of formation of 2-picoline to 4-picoline | 1.55 | 1.65 | 1.65 | 1.70 | 1.65 |
| Regeneration time (hr) | 2.0 | 2.5 | 3.0 | 3.0 | 3.0 |

EXAMPLE 11

An aqueous sodium silicate solution was neutralized with sulfuric acid, and an aqueous aluminum nitrate solution was added to the precipitated silica gel. Ammonia water was added thereto, while stirring the solution, and aluminum hydroxide was thereby precipitated, filtered and washed with water. The water-washed cake was admixed with water, and an aqueous manganese sulfate solution and an aqueous potassium fluoride solution were added thereto, while stirring the solution, and manganese fluoride was thereby precipitated, filtered, dried and then fired at 500°C for 4 hours, whereby the powders having a composition of 75 % $SiO_2$ — 16 % $Al_2O_3$ — 9 % $MnF_2$ was obtained.

200 g of the thus obtained powders and 300 g of powders of $Co_3Al_5(PO_4)_7$ prepared in Example 9, the latter being impregnated with 600 g of an aqueous solution of 3 % by weight of triammonium phosphate were mixed together and molded to pellets having diameters of 3 mm. 500 cc of the thus prepared pellets was packed in the same reactor tube as in Example 1, and reactions and regenerations were repeated five times under the same reaction and regeneration conditions as in Example 1. The results are shown in Table 21.

For comparison, 200 g of the powders of 75 % $SiO_2$ — 16 % $Al_2O_3$ — 9 % $MnF_2$, and 300 g of the powders of $Co_3Al_5(PO_4)_7$ without any impregnation with the aqueous triammonium phosphate solution were mixed together and used as a catalyst. The results are shown in Table 22.

Table 21

| Yields | 1st | 2nd | Reaction Run 3rd | 4th | 5th |
|---|---|---|---|---|---|
| pyridine | 2.0 % | 2.2 % | 2.4 % | 2.1 % | 2.2 % |
| 2-picoline | 36.5 " | 36.4 " | 35.9 " | 35.9 " | 36.3 " |
| 4-picoline | 17.4 " | 17.3 " | 16.9 " | 17.2 " | 17.1 " |
| 2-methyl-3-ethyl-pyridine | 3.5 " | 3.7 " | 3.5 " | 3.9 " | 3.8 " |
| 2-methyl-5-ethyl-pyridine | 6.1 " | 5.9 " | 5.9 " | 5.7 " | 6.2 " |
| Overall yield | 65.5 % | 65.5 % | 64.6 % | 64.8 % | 65.6 % |
| Ratio of formation of 2-picoline to 4-picoline | 2.1 | 2.1 | 2.1 | 2.1 | 2.1 |
| Regeneration time (hr) | 2.0 | 2.5 | 2.5 | 2.5 | 2.5 |

Table 22

| Yields | 1st | 2nd | Reaction Run 3rd | 4th | 5th |
|---|---|---|---|---|---|
| pyridine | 1.9 % | 1.5 % | 1.5 % | 1.3 % | 1.1 % |
| 2-picoline | 35.8 " | 34.0 " | 32.6 " | 31.9 " | 30.3 " |
| 4-picoline | 16.7 " | 15.5 " | 15.5 " | 15.1 " | 14.1 " |
| 2-methyl-3-ethyl- | | | | | |

Table 22-continued

| Yields | 1st | 2nd | Reaction Run 3rd | 4th | 5th |
|---|---|---|---|---|---|
| pyridine | 3.3 " | 3.1 " | 2.8 " | 2.7 " | 2.4 " |
| 2-methyl-5-ethyl-pyridine | 5.7 " | 5.5 " | 5.1 " | 4.9 " | 4.4 " |
| Overall yield | 63.4 % | 59.6 % | 57.5 % | 55.9 % | 52.3 % |
| Ratio of formation of 2-picoline to 4-picoline | 2.15 | 2.2 | 2.1 | 2.1 | 2.15 |
| Regeneration time (hr) | 3.0 | 3.5 | 3.5 | 3.5 | 3.5 |

EXAMPLE 12

$Co_3Al_2(PO_4)_4$ was prepared in the same manner as in Example 1, thoroughly water-washed and dried. 500 g of the dried $Co_3Al_2(PO_4)_4$ was impregnated with 300 g of an aqueous solution of 3 % by weight of phosphoric acid, dried and molded to pellets having diameters of 3 mm. 500 cc of the thus prepared pellets was packed in the same reactor tube as in Example 1 as a catalyst, and 372 g/hr of acetaldehyde containing 22 g of an aqueous 37 % formaldehyde solution and 140 g/hr of ammonia, which were preheated to 400°C separately, were mixed and the resulting gas mixture was passed through the reactor tube while keeping the reactor tube at 450°C.

The product liquid was cooled, collected and thoroughly dehydrated with flaky caustic soda. Then, the product liquid was fractionated in a distilling column. After the completion of the reaction, $N_2$ gas was passed through the reactor tube to flush the reactor tube thoroughly. Then, a gas mixture of airsteam was passed to the reactor tube and the carbonanceous materials deposited on the catalyst during the reaction was combusted at a temperature of 500° to 520°C to regenerate the catalyst activity. Such reaction and regeneration were repeated five times, and the yields and ratios of formation of 2-picoline to 4-picoline are shown in Table 23.

For comparison, $Co_3Al_2(PO_4)_4$ without any impregnation with the aqueous phosphoric acid solution was used as a catalyst. The results are shown in Table 24.

Table 23

| Yields | 1st | 2nd | Reaction Run 3rd | 4th | 5th |
|---|---|---|---|---|---|
| pyridine | 5.4 % | 5.8 % | 5.2 % | 5.7 % | 5.3 % |
| 2-picoline | 37.8 " | 37.2 " | 38.3 " | 37.6 " | 37.2 " |
| 4-picoline | 8.8 " | 8.5 " | 8.7 " | 8.5 " | 8.4 " |
| 2-methyl-3-ethyl-pyridine | 3.7 " | 3.9 " | 3.5 " | 3.4 " | 3.6 " |
| 2-methyl-5-ethyl-pyridine | 5.8 " | 6.1 " | 6.2 " | 5.7 " | 6.0 " |
| Overall yield | 61.5 % | 61.5 % | 61.9 % | 60.9 % | 60.5 % |
| Ratio of formation of 2-picoline to 4-picoline | 4.3 | 4.4 | 4.4 | 4.4 | 4.4 |
| Regeneration time (hr) | 3.5 | 4.0 | 4.0 | 4.0 | 4.0 |

Table 24

| Yields | 1st | 2nd | Reaction Run 3rd | 4th | 5th |
|---|---|---|---|---|---|
| pyridine | 5.6 % | 5.3 % | 5.0 % | 4.4 % | 4.0 % |
| 2-picoline | 36.7 " | 35.2 " | 34.0 " | 32.7 " | 30.9 " |
| 4-picoline | 8.1 " | 8.0 " | 7.7 " | 7.4 " | 6.8 " |
| 2-methyl-3-ethyl-pyridine | 3.6 " | 3.3 " | 3.1 " | 2.9 " | 2.7 " |
| 2-methyl-5-ethyl-pyridine | 5.6 " | 5.3 " | 4.7 " | 8.5 " | 4.2 " |
| Overall yield | 59.6 % | 57.1 % | 54.5 % | 51.9 % | 48.6 % |
| Ratio of formation of 2-picoline to 4-picoline | 4.5 | 4.4 | 4.4 | 4.4 | 4.5 |
| Regeneration time (hr) | 4.5 | 5.0 | 5.0 | 5.0 | 5.0 |

EXAMPLE 13

4,000 g of an aqueous solution of 10 % by weight of sodium silicate was neutralized with sulfuric acid, and 2,760 g of an aqueous solution of 10 % by weight of aluminum nitrate and 600 g of an aqueous solution of 10 % by weight of cadmium nitrate were added to the precipitated silica gel. Ammonia water was added thereto while thoroughly stirring the solution, and silica-alumina gel containing cadmium oxide and having a composition of 80 % $SiO_2$ — 15 % $Al_2O_3$ — 5 % CdO was precipitated.

On the other hand, 5,000 g of an aqueous solution containing 5.8 moles of diammonium monohydrogenphosphate and 9,500 g of an aqueous solution containing 3 moles of cobalt nitrate and 3 moles of aluminum nitrate were mixed together at a temperature of 50°C instantaneously, and at the same time ammonia water was added thereto to neutralize the solution. Gel of a phosphate of two metals having a composition of $Co_3Al_3(PO_4)_5$ was precipitated.

To the gel solution of $Co_3Al_3(PO_4)_5$ was added silica-alumina gel containing cadmium oxide at a ratio of the former to the latter of 7 : 3 by weight. After thorough mixing, the gel was waterwashed, dried, molded to pellets having diameters of 3 mm and fired at 500°C for 2 hours. 500 g of the thus prepared catalyst was impregnated with 300 g of an aqueous solution of 5 % by weight of diammonium monohydrogenphosphate. 500 cc of the thus impregnated catalyst was packed in the same reactor tube as in Example 1, and reactions and regenerations were repeated 5 times under the same reaction and regeneration conditions as in Example 1. The results are shown in Table 25.

For comparison, the catalyst without any impregnation with the aqueous diammonium monohydrogenphosphate solution was used, and the results are shown in Table 26.

Table 25

| Yields | Reaction Run | | | | |
|---|---|---|---|---|---|
| | 1st | 2nd | 3rd | 4th | 5th |
| pyridine | 2 % | 2.3 % | 2.5 % | 1.7 % | 2.1 % |
| 2-picoline | 38.1 " | 37.6 " | 38.2 " | 39.4 " | 39.0 " |
| 4-picoline | 19.8 " | 18.9 " | 18.8 " | 19.0 " | 18.7 " |
| 2-methyl-3-ethyl-pyridine | 3.8 " | 4.2 " | 3.7 " | 4.0 " | 3.7 " |
| 2-methyl-5-ethyl-pyridine | 5.8 " | 6.1 " | 5.5 " | 5.5 " | 6.1 " |
| Overall yield | 69.5 % | 69.1 % | 68.7 % | 69.6 % | 69.6 % |
| Ratio of formation of 2-picoline to 4-picoline | 2.0 | 2.0 | 2.0 | 2.1 | 2.1 |
| Regeneration time (hr) | 2 | 2.5 | 2.5 | 2.5 | 2.5 |

Table 26

| Yields | Reaction Run | | | | |
|---|---|---|---|---|---|
| | 1st | 2nd | 3rd | 4th | 5th |
| pyridine | 1.8 % | 1.5 % | 1.4 % | 1.0 % | 1.0 % |
| 2-picoline | 37.0 " | 36.2 " | 34.9 " | 33.2 " | 31.8 " |
| 4-picoline | 18.5 " | 17.7 " | 17.0 " | 16.2 " | 15.2 " |
| 2-methyl-3-ethyl-pyridine | 3.6 " | 3.5 " | 3.3 " | 3.0 " | 2.9 " |
| 2-methyl-5-ethyl-pyridine | 5.7 " | 5.2 " | 5.3 " | 4.9 " | 4.9 " |
| Overall yield | 66.6 % | 64.1 % | 61.9 % | 58.3 % | 55.8 % |
| Ratio of formation of 2-picoline to 4-picoline | 2.0 | 2.05 | 2.05 | 2.05 | 2.1 |
| Regeneration time (hr) | 3 | 3.5 | 3.5 | 3.5 | 3.5 |

What is claimed is:

1. A method for producing 2-picoline and 4-picoline comprising
   catalytically reacting acetaldehyde
   with ammonia
   in the gaseous phase
   in the presence of a catalyst of at least one phosphate selected from the group consisting of cobalt magnesium phosphate, cobalt aluminum phosphate and lead aluminum phosphate which has been impregnated with 1% to 30% by weight of phosphoric acid or ammonium phosphate
   in state of aqueous solution,
   at a temperature of from 350° C. to 500° C. and
   a space velocity of 200 $Hr^{+1}$ to 2000 $Hr^{+1}$.

2. A method according to claim 1 wherein said phosphate is cobalt aluminum phosphate and said cobalt aluminum phosphate is $Co_3Al_2(PO_4)_4$, $Co_3Al_3(PO_4)_5$, $Co_3Al_5(PO_4)_7$ or $Co_3Al(PO_4)_3$.

3. A method according to claim 1 wherein said phosphate is lead aluminum phosphate and said lead aluminum phosphate is $Pb_3Al_5(PO_4)_7$.

4. A method according to claim 1 wherein said phosphate is cobalt magnesium phosphate and and said cobalt magnesium phosphate is $Co_3Mg_3(PO_4)_4$.

5. A method according to claim 1 wherein the catalyst further comprises silica-alumina.

6. A method according to claim 5 wherein said silica alumina is blended with at least one oxide selected from zinc oxide and cadmium oxide.

7. A method according to claim 5 wherein said silica alumina is blended with at least one fluoride selected from manganese fluoride, lead fluoride and bismuth fluoride.

8. A method according to claim 5 wherein said silica alumina is blended with at least one oxide selected from zinc oxide and cadmium oxide, and at least one fluoride selected from manganese fluoride, lead fluoride and bismuth fluoride.

9. A method according to claim 1 wherein said ammonium phosphate is triammonium phosphate, diammonium monohydrogenphosphate, and monoammonium dihydrogenphosphate.

10. A method according to claim 1 wherein the aqueous phosphoric acid solution has concentration of from 1 to 25 % by weight.

11. A method according to claim 9 wherein the aqueous ammonium phosphate solution has concentration of from 1 to 25 % by weight.

12. A method according to claim 1 wherein a molar ratio of acetaldehyde to ammonia is 0.3 to 3.

* * * * *